United States Patent [19]

Heckelsberg

[11] 4,093,536

[45] June 6, 1978

[54] CATALYTIC CRACKING AND DEHYDROCYCLIZING OF ALKANES USING ALKALINE EARTH OXIDES PROMOTED WITH MANGANESE OXIDE AND/OR RHENIUM OXIDE

[75] Inventor: Louis F. Heckelsberg, Bartlesville, Okla.

[73] Assignee: Phillips Petroleum Company, Bartlesville, Okla.

[21] Appl. No.: 580,010

[22] Filed: May 22, 1975

Related U.S. Application Data

[63] Continuation-in-part of Ser. No. 460,935, Apr. 15, 1974, abandoned.

[51] Int. Cl.$^2$ .................... C10G 11/04; B01J 27/04
[52] U.S. Cl. .................... 208/121; 208/108; 208/134; 208/141; 208/213; 208/226; 252/471; 252/475; 260/673; 260/673.5
[58] Field of Search .............. 208/121, 134, 141, 143, 208/144, 145, 108, 112; 260/668 R, 673, 673.5, 676, 683.2, 683.3, 683.65; 252/471; 423/213.2, 245

[56] References Cited

U.S. PATENT DOCUMENTS

| | | | |
|---|---|---|---|
| 2,378,209 | 6/1945 | Fuller et al. | 260/668 R |
| 2,627,506 | 2/1953 | Hunter et al. | 252/463 |
| 2,848,510 | 8/1958 | Myers et al. | 260/668 R |
| 3,280,040 | 10/1966 | Jaffe | 252/439 |
| 3,308,187 | 3/1967 | Bajars | 260/680 |
| 3,308,192 | 3/1967 | Bajars | 260/680 |
| 3,308,199 | 3/1967 | Bajars | 260/680 |
| 3,388,074 | 6/1968 | Reitmeier | 252/373 |
| 3,410,787 | 11/1968 | Kubicek | 208/57 |
| 3,501,395 | 3/1970 | Miale | 208/112 |
| 3,509,041 | 4/1970 | Miale | 208/110 |
| 3,575,848 | 4/1971 | Miale | 208/112 |
| 3,584,060 | 6/1971 | Rausch | 260/669 |
| 3,649,564 | 3/1972 | Hayes | 252/466 PT |
| 3,649,566 | 3/1972 | Hayes et al. | 252/470 |
| 3,725,495 | 4/1973 | Wrisberg et al. | 260/683 R |
| 3,929,670 | 12/1975 | Kudo et al. | 252/462 X |

*Primary Examiner*—Delbert E. Gantz
*Assistant Examiner*—G. E. Schmitkons

[57] ABSTRACT

Alkanes are catalytically converted employing a catalyst comprising at least one alkaline earth oxide together with a promoting amount of manganese oxide and/or rhenium oxide. When the catalyst is treated with an oxygen-containing gas, such as air, prior to contacting the alkanes conversion by cracking is favored. When the catalyst is treated with hydrogen prior to contacting the alkanes dehydrocyclization is favored. A composition of matter is disclosed suitable for use as a catalyst for converting alkanes.

11 Claims, No Drawings

CATALYTIC CRACKING AND DEHYDROCYCLIZING OF ALKANES USING ALKALINE EARTH OXIDES PROMOTED WITH MANGANESE OXIDE AND/OR RHENIUM OXIDE

RELATED APPLICATION

This application is a continuation in part of my copending application Ser. No. 460,935 filed Apr. 15, 1974, now abandoned.

BACKGROUND OF THE INVENTION

The invention relates to a composition of matter suitable as a catalyst, and a method for converting alkanes, including a method for cracking alkanes using the catalyst and a method for dehydrocyclizing alkanes using the catalyst.

Catalytic cracking and dehydrocyclizing of various hydrocarbons constitute a very important part of most refining operations. Although many catalysts are known for such processes, catalytic cracking and dehydrocyclizing are areas of continuing research in an effort to find new and better processes and catalysts.

An object of the invention is to crack alkanes.

Another object of the invention is to dehydrocyclize alkanes.

Another object of the invention is to crack or dehydrocyclize alkanes using a catalyst.

Still another object of the invention is to provide a catalyst suitable for cracking alkanes or dehydrocyclizing alkanes.

Other objects, aspects, and advantages of the invention will be apparent to those skilled in the art upon studying the specification and the appended claims.

SUMMARY

According to the invention, a composition of matter is provided comprising at least one alkaline earth oxide together with a promoting amount of a compound selected from the group consisting of manganese oxide and rhenium oxide.

Further, according to the invention, alkanes are converted employing a catalyst of the above composition.

Further, according to the invention, alkanes are catalytically cracked employing a catalyst comprising at least one alkaline earth oxide together with a promoting amount of a compound selected from the group consisting of manganese oxide and rhenium oxide wherein said catalyst is treated with a dry oxygen containing gas at a high temperature prior to contacting the alkanes.

Still further, according to the invention, alkanes are catalytically dehydrocyclized employing a catalyst comprising at least one alkaline earth oxide together with a promoting amount of a compound selected from the group consisting of manganese oxide and rhenium oxide wherein said catalyst is treated with hydrogen at a high temperature prior to contacting the alkanes.

DETAILED DESCRIPTION OF THE INVENTION

Alkaline earth oxides, namely the oxides of magnesium, calcium, strontium, and barium, are useful in this invention. Oxides of magnesium, calcium and strontium are especially useful. A single oxide, such as calcium oxide, can be promoted with manganese oxide and/or rhenium oxide; or mixtures of alkaline earth oxides, such as magnesium oxide and calcium oxide or magnesium oxide and strontium oxide, can be promoted with manganese oxide and/or rhenium oxide.

The proportions of the alkaline earth oxides where more than one alkaline earth oxide is employed is not believed to be critical. For the dehydrocyclization embodiment magnesium oxide and calcium oxide in weight ratios of from 100/1 to 5/1 produced good results and are preferred. For the embodiment wherein alkanes are cracked the best results were obtained using a mixture of magnesium oxide and either calcium oxide or strontium oxide in approximately 20/1 to 8/1 weight ratio with a promoter. Where one alkaline oxide was used with a promoter to crack alkanes, the best results were obtained using calcium oxide.

Oxides of either manganese and/or rhenium are useful as promoters for the above described catalysts. While it is recognized that both manganese and rhenium are capable of existing in a range of oxidation states, the precise nature of the promoting species of this invention has not been determined. One skilled in the art, after examination of the preparation procedure for the cracking catalyst, will readily recognize that the promoting species of this invention are undoubtedly among the higher oxidation states available for manganese or rhenium. In the case of the dehydrocyclization catalyst, the hydrogen treatment may reduce the manganese and rhenium. For sake of simplicity and ease of calculation the promoting species for both the cracking and dehydrocyclization catalyst are hereinafter referred to as $Mn_2O_7$ and $Re_2O_7$, although it is recognized that the actual promoted catalyst is the reaction product resulting from the admixture, under suitable catalyst-forming and catalyst-activating conditions, of suitable alkaline earth metal compounds and manganese and/or rhenium compounds.

It is not presently believed that the amount of promoter employed is critical. From 0.1 to 30 parts by weight of the promoting compound per 100 parts by weight alkaline earth oxide or mixture thereof is generally adequate to produce the desired results. It is currently preferred to use in the range of from about 1 to 15 parts by weight promoter per 100 parts by weight alkaline earth oxides since good results were obtained employing this range.

The catalyst system including promoter and alkaline earth oxide(s) can be prepared by any convenient means such as dry blending, slurry blending, solution blending, etc. In the preparation of the inventive catalysts, oxides of manganese and/or rhenium and alkaline earth metals, or compounds of these elements which are convertible to the oxide on calcination, are combined in any suitable catalyst-forming method. The catalysts can be in any suitable form, such as pellets, pills, agglomerates, and powders. Before use, the catalyst is heated under a stream of the appropriate treating agent or gas as described herein at a temperature ranging from about 750° to about 1200° F (about 400°–650° C) for a period of time ranging from about 0.1 to about 20 hours.

Where the cracking of alkanes is to be favored according to one embodiment of the invention, the catalyst above described is treated with a dry oxygen-containing gas. Where the dehydrocyclization of alkanes is to be favored according to another embodiment of the invention, the catalyst above described is treated with hydrogen. The hydrogen treatment can either replace the oxygen-containing gas treatment or the hydrogen treatment can follow the oxygen-containing gas treatment. Whichever treating gas is used, it is frequently considered beneficial to flush the treated catalyst with an inert gas such as nitrogen prior to contact with the feed.

It is pointed out that whether the catalyst is treated with a dry oxygen-containing gas or hydrogen, reactions carried out employing such catalysts involve both cracking and dehydrocyclization reactions. The hydrogen treatment of the catalyst enhances the dehydrocyclization activity of the catalyst, but the hydrogen-treated catalyst also produces a substantial quantity of cracked products.

It is currently convenient to prepare the catalyst according to the following procedure. A weighed amount of an oxide, such as magnesium oxide, is slurried with a water solution containing the appropriate amount of a nitrate of another alkaline earth metal, such as calcium nitrate or strontium nitrate. After evaporation of the water from the slurry, the dried solid is re-slurried with a water solution of an appropriate nitrate as for example, manganese (II) nitrate or rhenium (II) nitrate. After evaporation of the water from the slurry, the dried solid is ground, sieved and treated with a dry oxygen containing gas or hydrogen at a temperature ranging from about 950° to about 1050° F (510° to about 566° C) for a period of time ranging from about 1 to about 4 hours. Good results were obtained by treating the catalyst at a temperature of 1000° F (538° C) for 4 hours. The above procedure describes the preparation of a catalyst containing a mixture of alkaline earth oxides. When a single alkaline earth oxide is desired, the slurrying with the alkaline earth nitrate solution is omitted. Rhenium is applied to the catalyst as described above except that an aqueous solution of ammonium perrhenate is used.

Feedstocks capable of being cracked by the catalyst system of this invention include any of the normal cracking feedstocks containing linear or branched saturated hydrocarbons referred to generally as alkanes. These can be crude oil fractions or other refinery streams. The desired mixture of products will generally determine the selection of feedstock. For example, one feedstock may be more suitable to produce gasoline than another.

Feedstocks capable of undergoing dehydrocyclization in the presence of the catalyst system of this invention include any of the above-described feeds containing substantial quantities of linear or branched saturated alkanes containing 6 or more carbon atoms per molecule. Preferred alkane components of the feedstock contain carbon chains of 6 or more carbon atoms in a chain either unsubstituted or substituted with one or more alkyl side chains. Of course, the products obtained employing either the cracking or dehydrocyclization embodiments of the invention are dependent on the feedstock to a large extent.

Any type of reactor normally used in catalytic cracking or dehydrocyclizing operations can be used with the catalyst system of this invention. For example, fixed bed, fluidized bed, trickle bed, etc., reactors can be employed, though fluidized bed reactors are usually used in commercial processes.

Reaction conditions suitable for catalytic cracking or dehydrocyclization vary widely. The reaction conditions depend to some extent upon the feedstock and the desired products. Temperatures are normally in the range of from about 450° to about 600° C (842° to about 1112° F), although temperatures from about 525° to about 575° C (977° to about 1067° F) have produced good results. Space velocity of feedstock is dependent to a large extent upon the specific conditions such as feedstock, temperature, diluent, desired products, ets., but a space velocity sufficient to provide a contact time of 0.1–50 seconds is generally desirable. Pressures are ordinarily near atmospheric but pressures in the range of from about 0–200 psig can be used.

It may be desirable in some cases to employ a diluent. Inert diluents such as nitrogen may be used, or it may be advantageous to use hydrogen gas to control dehydrogenation, coke formation, and product distribution.

It is often advantageous to periodically regenerate the catalyst bed by any suitable means, such as treatment with dry air at elevated temperatures. Such regeneration generally removes deposits of coke which can be formed in varying amounts during the cracking or dehydrocyclization reaction.

EXAMPLES

In the following examples a pulse-type reactor was employed. The reactor was 1 cm O.D. by 30.5 cm long which included a catalyst bed approximately 3 cm long. The analyzer was a gas-liquid chromatograph (glc). A feed injector introduced 3 to 5 microliter pulses of feedstock into the reactor at desired time intervals and temperatures. The catalysts were prepared employing the slurry blending as herein described.

EXAMPLE I

In this example n-heptane was cracked to produce $C_1$ to $C_3$ products employing various catalysts of the invention. The amount of catalyst used was varied and so was the temperature of the process. Several runs at various temperatures were made employing a reactor without a catalyst and employing a reactor containing only quartz to establish a basis for comparison of the results employing the inventive catalysts. The reactor was initially flushed with dry air at 1000° F (538° C) for 4 hours and then with helium at 3–5 psig for 15 minutes prior to introducing the feed into the reactor. Air was allowed to flow through the reactor at the desired reaction temperature for 30 minutes between feed pulses. Residence time of feed in the reactor was approximately 1 second and the pressure was 3 psig. The reaction temperature, catalyst, catalyst amount, catalyst weight ratio, and results are provided in Table I. In this example and the following examples conversion represents weight percent of feed converted into $C_1$ to $C_3$ products including minor amounts of hydrogen gas. Also selectively represents weight percent of feed converted into volatile products.

TABLE I

Cracking of n-Heptane

| Catalyst | None | Quartz | CaO/Mn$_2$O$_7$ | | CaO/Mn$_2$O$_7$ | | MgO/Mn$_2$O$_7$ | MgO/CaO/Mn$_2$O$_7$ | | MgO/SrO/Mn$_2$O$_7$ | | MgO/CaO/Mn$_2$O$_7$ | MgO/CaO/Mn$_2$O$_7$ | CaO/Re$_2$O$_7$ |
|---|---|---|---|---|---|---|---|---|---|---|---|---|---|---|
| Wt. Ratio | | | 95/5 | | 9/1 | | 95/5 | 90/9/1 | | 90/9/1 | | 88/9/3 | 85/10/5 | 95/5 |
| Amount | | | 1 ml | 2 ml | 1 ml | 2 ml | 1 ml | 1 ml | 2 ml | 1 ml | 2 ml | 1 ml | 1 ml | 2 ml |
| Temp. °C | | | | | | | | | | | | | | |
| 450 Conversion | 23[a] | 22[a] | | | | | 37 | | | | | | | |
| 450 Selectivity | | | | | | | 8[a] | | | | | | | |
| 500 Conversion | 2 | 2 | 7 | 11 | 12 | 17 | 70 | 8 | | 6 | | | | 4 |
| 500 Selectivity | 77 | 82 | 75 | 73 | 81 | 78 | 51[a] | 81 | | 80 | | | | 84 |
| 525 Conversion | 5 | 6 | | | 22 | | | 15 | | 11 | | 15 | 12 | |
| 525 Selectivity | 76 | 76 | | | 82 | | | 82 | | 83 | | 85 | 80 | |
| 550 Conversion | 11 | 15 | 21 | 29 | 32 | 30 | 85 | 25 | 24 | 20 | 45 | 25 | 20 | 20 |
| 550 Selectivity | 78 | 78 | 78 | 78 | 84 | 82 | 36 | 83 | 87 | 82 | 90 | 86 | 82 | 89 |
| 575 Conversion | 26 | 18 | | | 50 | | | 39 | | 34 | 46 | 38 | 34 | 37 |
| 575 Selectivity | 80 | 82 | | | 87 | | | 84 | | 85 | 86 | 87 | 86 | 85 |

[a]Major amount of hydrogen formed. Not included in selectivity.

The above runs establish the operability of the invention. Most of the inventive runs showed a substantial improvement in both conversion and selectivity over the runs employing a reactor without a catalyst or containing only quartz, particularly at the higher cracking temperatures.

EXAMPLE II

Another series of runs was made identical to the conditions used in Example I with the exception that the feed was 3-methylhexane. Results are shown in Table II.

TABLE II

Cracking of 3-Methylhexane

| Catalyst | | None | Quartz | CaO/Mn$_2$O$_7$ | | CaO/Mn$_2$O$_7$ | CaO/Re$_2$O$_7$ | MgO/CaO/Mn$_2$O$_7$ | MgO/SrO/Mn$_2$O$_7$ | |
|---|---|---|---|---|---|---|---|---|---|---|
| Wt. Ratio | | | | 95/5 | | 9/1 | 95/5 | 90/9/1 | 90/9/1 | |
| Amount | Temp., °C | | 1 ml | 1 ml | 2 ml | 2 ml | 2 ml | 1 ml | 1 ml | 2 ml |
| Conversion % | 500 | | | | | | | 6 | 6 | |
| Selectivity % | | | | | | | | 90 | 86 | |
| Conversion % | 525 | | | | | | | 9 | | |
| Selectivity % | | | | | | | | 87 | | |
| Conversion % | 550 | 13 | 14 | 20 | | 23 | 19 | 20 | 18 | 37 |
| Selectivity % | | 70 | 72 | 80 | | 83 | 93 | 86 | 85 | 90 |
| Conversion % | 575 | | | | | | | 33 | 34 | |
| Selectivity % | | | | | | | | 87 | 86 | |

The above results were consistent with the results of Example I.

EXAMPLE III

Additional runs were made employing either 2,3,3-trimethylbutane or 2,4-dimethylpentane as the feed. The reaction conditions were the same as in the previous examples. The results are given in Table III.

TABLE III

Cracking of 2,2,3-Trimethylbutane and 2,4-Dimethylpentane

| | | 2,2,3-Trimethylbutane | | | | | 2,4-Dimethylpentane | | |
|---|---|---|---|---|---|---|---|---|---|
| Catalyst | | | CaO/Mn$_2$O$_7$ | MgO/CaO/ Mn$_2$O$_7$ | MgO/SrO/ Mn$_2$O$_7$ | | | MgO/CaO/ Mn$_2$O$_7$ | MgO/SrO/ Mn$_2$O$_7$ |
| Wt. Ratio | | | 9/1 | 90/9/1 | 90/9/1 | | | 90/9/1 | 90/9/1 |
| Amount | | None | 1 ml | 1 ml | 1 ml | None | | 1 ml | 1 ml |
| Run No. | Temp., °C | Run 1 | Run 2 | Run 3 | Run 4 | Run 5 | Run 6 | Run 7 | Run 8 | Run 9 |
| Conversion, % | 500 | 4 | 11 | 13 | 11 | 7 | 3 | 9 | 4 | 4 |
| Selectivity, % | | | 61 | 65 | 69 | 83 | 72 | 54 | 79 | 68 | 66 |
| Conversion, % | 525 | 12 24 | 27 | 12 | 13 | 8 | 21 | 8 | 9 | |
| Selectivity, % | | | 63 | 65 | 65 | 66 | 61 | 56 | 62 | 68 | 65 |
| Conversion, % | 550 | 27 | 36 | 48 | 26 | 26 | 16 | 32 | 18 | 17 |
| Selectivity, % | | | 58 | 66 | 64 | 65 | 59 | 59 | 64 | 69 | 65 |
| Conversion, % | 575 | 48 | 54 | 72 | 49 | 45 | 27 | 44 | 34 | 33 |
| Selectivity, % | | | 59 | 70 | 68 | 67 | 61 | 63 | 67 | 71 | 69 |

The above results were consistent with the results of Examples I and II. Although it was not determined why a discrepancy existed between the results in runs 3 and 4 and in runs 7 and 8, it is noted that selectivity was better in the runs in which the inventive catalyst was used as compared to the runs in which no catalyst was used.

EXAMPLE IV

This example illustrates the dehydrocyclization embodiment of this invention.

A catalyst corresponding to CaO/Mn$_2$O$_7$/MgO in the weight ratio 3/7/90, respectively, was prepared as described earlier by impregnating MgO with aqueous solutions of calcium nitrate followed by manganous nitrate. After drying, grinding and sieving the catalyst was treated with hydrogen gas or dry air at 1000° F (538° C) for 1 hour followed by nitrogen gas for 5 minutes. Passing n-heptane over the thus-prepared catalysts at 1022° F (550° C) and atmospheric pressure at a rate of 1 gm feed per 1 ml catalyst per hour gave the results tabulated in Table IV.

Table IV

Dehydrocyclization of n-Heptane

| | Catalyst Treatment | |
|---|---|---|
| | Hydrogen | Air |
| n-Heptane conversion, %[a] | 21.8 | 14.5 |
| Aromatics selectivity, %[b] | 20 | 2 |
| Cracking selectivity, %[c] | 80 | 98 |

[a]Conversion to products.
[b]Predominantly toluene.
[c]Percent of total volatile organic products containing less than 7 carbon atoms.

These data show that substantial amounts of aromatic products, especially toluene, are formed from n-heptane by use of the inventive process. These results also show that hydrogen-treatment results in higher conversion to products and higher selectivity to aromatics than does treatment with an oxygen containing gas.

EXAMPLE V

This example illustrates the dehydrocyclization embodiment of the invention utilizing catalysts of varying composition.

Catalysts corresponding to CaO/Mn$_2$O$_7$/MgO in various weight ratios were prepared and treated with hydrogen as described in Example IV. n-Heptane was utilized as feed through the reactor at conditions of temperature, pressure and feed rate as described in Example IV. Data are recorded in Table V.

Table V

Varying Catalyst Composition

| CaO/Mn$_2$O$_7$/MgO | n-Heptane Conv., % | Aromatic Select., % | Cracking Select., % |
|---|---|---|---|
| 1/9/90 | 24 | 31 | 69 |
| 3/7/90 | 30 | 9(95)[a] | [a] |
| 2.5/2.5/95 | 18 | 15 | 85 |
| 5/5/90 | 20 | 14 | 86 |
| 7.5/7.5/85 | 19 | 26 | 74 |
| 7/3/90 | 21 | 15 | 85 |

Table V-continued

| Varying Catalyst Composition | | | |
|---|---|---|---|
| CaO/Mn$_2$O$_7$/MgO | n-Heptane Conv., % | Aromatic Select., % | Cracking Select., % |
| 9/1/90 | 9 | b | b |

*Anomalous and inconsistent results not explained.
bInformation not available.

The above data show that a wide range of compositions containing CaO, Mn$_2$O$_7$ and MgO are useful in the dehydrocyclization embodiment of the invention.

EXAMPLE VI

This example illustrates the dehydrocyclization embodiment of the invention utilizing the catalyst and treatment thereof and reaction conditions as described in Example IV. Compounds with 6 or 7 carbon atoms and containing C$_4$ to C$_7$ carbon chains were utilized as feedstock. Data are tabulated in Table VI.

Table VI

| Feedstock | Variable Feedstock | | |
|---|---|---|---|
| | Conv., % | Aromatic Select., % | Cracking Select., % |
| n-Heptane | 25.0 | 9.4 | 90.6 |
| 2-Methylhexane | 23.1 | 11.0 | 89.0 |
| 3-Methylhexane | 26.6 | 9.1 | 90.9 |
| 2,2-Dimethylpentane | 24.9 | 1.0 | 99.0 |
| 2,3-Dimethylpentane | 29.3 | 1.9 | 98.1 |
| 2,4-Dimethylpentane | 20.5 | 2.1 | 97.9 |
| 2,2,3-Trimethylbutane | 26.2 | 0.8 | 99.2 |

These data illustrate that various feeds are useful in obtaining aromatic products, but those containing carbon chains of 6 or more carbon atoms provide higher selectivity to aromatics.

What is claimed is:

1. A method for catalytically converting alkanes comprising contacting the alkanes under converting conditions with a catalyst by forming a reaction mixture consisting essentially of said alkanes and a catalyst consisting essentially of components selected from the group consisting of:
   (A) two alkaline earth oxides and a promoting amount of a promoter selected from the group consisting of manganese oxide and a mixture of manganese oxide and rhenium oxide,
   (B) at least one alkaline earth oxide and a promoting amount of rhenium oxide, and
   (C) an alkaline earth oxide selected from the group consisting of strontium and barium and a promoting amount of a promoter selected from the group consisting of manganese oxide and a mixture of manganese oxide and rhenium oxide.

2. The method of claim 1 wherein the promoting amount is in the range of from about 0.1 to about 30 parts by weight per 100 parts by weight alkaline earth oxide.

3. The method of claim 1 wherein the promoting amount is in the range of from about 1 to about 15 parts by weight per 100 parts by weight alkaline earth oxide.

4. The method of claim 1 wherein the alkaline earth oxide in (A) and (B) is selected from the group consisting of magnesium, calcium, and strontium.

5. The method of claim 1 wherein the alkanes are catalytically cracked employing the catalyst which is treated with dry air at a temperature in the range of from about 750° to about 1200° F (approximately 400° to about 650° C) for a period of time ranging from about 0.1 hour to about 20 hours prior to contacting said alkanes.

6. The method of claim 5 wherein the cracking temperature is in the range of from about 450° to about 600° C (842° to about 1112° F); wherein the cracking pressure is in the range of from about 0 to about 200 psig; and wherein the feed-to-catalyst contact time is in the range of from about 0.1 to about 50 seconds.

7. The method of claim 5 wherein the alkaline earth oxide in (A) and (B) is a mixture of magnesium oxide and calcium or strontium oxide, the weight ratio of magnesium oxide to calcium or strontium oxide is in the range of from about 20:1 to about 8:1, and the catalyst is treated at a temperature ranging from about 950° to about 1050° F (510° to about 566° C) for a period of time ranging from about 1 to about 4 hours.

8. The method of claim 1 wherein the alkanes are catalytically dehydrocyclized employing the catalyst which is treated with hydrogen at a temperature in the range of from about 750° to about 1200° F (approximately 400° to about 650° C) for a period of time ranging from about 0.1 hour to about 20 hours prior to contacting said alkanes, and wherein said alkanes are linear or branched substituted or unsubstituted alkanes having 6 or more carbon atoms per molecule.

9. The method of claim 8 wherein the alkanes contain carbon chains of at least 6 carbon atoms, either unsubstituted or substituted with one or more alkyl side chains.

10. The method of claim 8 wherein the dehydrocyclization temperature is in the range of from about 450° to about 600° C (842° to about 1112° F); wherein the dehydrocyclization pressure is in the range of from about 0 to about 200 psig; and wherein the feed to catalyst contact time is in the range of from about 0.1 to about 50 seconds.

11. The method of claim 8 wherein the alkaline earth oxide in (A) and (B) is a mixture of magnesium oxide and calcium or strontium oxide, the weight ratio of the magnesium oxide to calcium or strontium oxide is in the range of from about 100:1 to about 5:1, and the catalyst is treated at a temperature ranging from about 950° to about 1050° F (510° to about 566° C) for a period of time ranging from about 1 to about 4 hours.

* * * * *